United States Patent [19]
Moring et al.

[11] Patent Number: 5,384,024
[45] Date of Patent: Jan. 24, 1995

[54] CAPILLARY ELECTROPHORESIS

[75] Inventors: Stephen E. Moring, San Mateo; Michael S. Albin, Mountain View; Reid B. Kowallis, San Carlos; Thomas E. Lee, Sunnyvale; Dennis E. Mead, Campbell; John H. Nickel, San Jose; Mark F. Oldham, Los Gatos; Richard T. Reel, Hayward, all of Calif.; Timothy S. Orpin, Montrose; Janice C. Woods, Emerald, both of Australia

[73] Assignee: Applied Biosystems, Inc, Foster City, Calif.

[21] Appl. No.: 850,764

[22] Filed: Mar. 13, 1992

[51] Int. Cl.6 .................. B01D 61/46; B01D 57/02; G01N 27/26
[52] U.S. Cl. .................. 204/299 R; 204/180.1; 204/300 R; 215/247; 215/355; 422/63; 422/64
[58] Field of Search ............ 204/299 R, 180.1, 300 R; 215/247, 355, D3; 422/63–65

[56] References Cited

U.S. PATENT DOCUMENTS

| | | | |
|---|---|---|---|
| 2,526,622 | 10/1950 | Martin | 215/355 |
| 2,579,724 | 12/1951 | Breakstone | 215/247 |
| 4,124,470 | 11/1978 | Dahms | 204/180.1 |
| 4,134,512 | 1/1979 | Nugent | 215/247 |
| 4,515,752 | 5/1985 | Miramanda | 215/355 X |
| 4,906,344 | 3/1990 | Hjerten | 204/299 R |
| 4,927,265 | 5/1990 | Brownlee | 356/73 |
| 4,981,801 | 1/1991 | Suzuki et al. | 422/64 X |
| 4,995,521 | 2/1991 | von Schuckmann | 215/355 X |
| 5,021,646 | 6/1991 | Weinberger et al. | 250/227.11 |
| 5,037,523 | 8/1991 | Weinberger et al. | 204/299 R |
| 5,045,172 | 9/1991 | Guzman | 204/299 R |
| 5,047,134 | 9/1991 | Weinberger et al. | 204/299 R |
| 5,053,115 | 10/1991 | Weinberger et al. | 204/299 R |
| 5,060,812 | 10/1991 | Ogle | 215/355 X |
| 5,066,382 | 11/1991 | Weinberger et al. | 204/299 R |
| 5,073,239 | 12/1991 | Hjerten | 204/180.1 |
| 5,074,982 | 12/1991 | Novotny et al. | 204/299 R X |
| 5,110,431 | 5/1992 | Morina | 204/299 R X |
| 5,126,025 | 6/1992 | Carson et al. | 204/180.1 |
| 5,131,997 | 7/1992 | Christianson et al. | 204/299 R |
| 5,141,609 | 8/1992 | Sweedler et al. | 204/180.1 |
| 5,169,511 | 12/1992 | Allington et al. | 204/299 R |
| 5,173,163 | 12/1992 | Tehrani | 204/180.1 X |
| 5,202,010 | 4/1993 | Guzman | 204/299 R |
| 5,221,448 | 6/1993 | Weinberger | 204/180.1 |
| 5,264,101 | 11/1993 | Demorest et al. | 204/299 R |
| 5,290,418 | 3/1994 | Menchen et al. | 204/299 R |

FOREIGN PATENT DOCUMENTS

| | | | |
|---|---|---|---|
| 0329341 | 8/1989 | European Pat. Off. | 204/299 R |
| 0371573 | 6/1990 | European Pat. Off. | 204/299 R |
| 0395796 | 11/1990 | European Pat. Off. | 204/299 R |

OTHER PUBLICATIONS

Tehrani et al., "High performance capillary electrophoresis using a modular system", pp. 32–40, Nov./Dec. 1989.

Honda et al., "Evaluation of an automatic siphonic sampler for capillary zone electrophoresis", J. of Chromatography, 404(2), 1987, 313–20.

Primary Examiner—Donald E. Czaja
Assistant Examiner—Milton I. Cano
Attorney, Agent, or Firm—Donald R. Boys; Joseph H. Smith

[57] ABSTRACT

An instrument for capillary electrophoresis has a vertically translatable carrier holding one end of the capillary and an electrode connected to a power supply, and a rotary carousel for presenting containers of sample and buffer solutions to a load position where the end of the capillary and the electrode may be inserted by operating the carrier. The other end of the capillary and a second electrode connected to the power supply are immersed in an outlet buffer reservoir. The instrument has a vacuum supply for providing a relative vacuum over the solution in the outlet buffer reservoir, so simple material may be injected into the capillary either by electromigration or by differential pressure. After injection, the first end of the capillary and the electrode may be immersed in buffer to accomplish electrophoresis. By manipulating the carousel and carrier, multiple samples may be electrophoresed in series. In a preferred embodiment the instrument includes a flexible duck-billed septum for closing containers while permitting easy access for the electrode and the capillary tube. Also in a preferred embodiment the instrument is controlled by a microprocessor-based controller.

26 Claims, 14 Drawing Sheets

CAPILLARY ELECTROPHORESIS

BACKGROUND OF THE INVENTION

The present system relates to systems for performing capillary electrophoresis and more particularly to apparatus for introducing samples into capillary columns for capillary electrophoresis and performing multiple electrophoretic sample analyses and methods development.

BACKGROUND OF THE INVENTION

In recent years significant advances have been made in micro-column separation techniques. A principle advantage of such techniques is their suitability for analysis of very small sample volumes, e.g. microliter or sub-microliter amounts of sample. Being able to analyze such small amount of sample has become very important because, oftentimes, the available volume of sample for analysis is extremely small. For example, in forensic and criminal investigations, the only material that may be available for analysis may comprise a fingernail scraping or a stain on an article of clothing.

An area of difficulty in micro-column electrophoresis is in sample introduction, particularly in view of tiny sample volumes to be introduced, and the ever-growing demand for analysis. One technique used is electromigration, a term including the effects of electrophoresis and electroendosmosis. This technique and the underlying principles are discussed in Jorgenson, J. W. and Lukacs, K. D., *J. Chromatography,* 1981, Vol. 218, pp. 209–216; Jorgenson, J. W. and Lukacs, K. D., Science, 1983, volume 222, pp 266–272; in Wailingford, R. A. and Ewing A. G., *Anal. Chem.,* 1987, Vol. 59, pp. 681–684.

In a typical electrophoresis process using a capillary, one end of the capillary is maintained in a buffer solution in a reservoir with an electrode also immersed in the buffer for providing one terminal from a power supply for maintaining an electrical potential across the length of the capillary. It is this electrical potential, eg. voltage, that is the driving force for electrophoresis. Typically, during the electrophoresis run, the opposite end of the capillary is also immersed in a buffer solution in a reservoir with a second electrode providing the second terminal from the power supply.

To introduce sample in such a process, it is necessary to remove one end of the capillary from its buffer reservoir and to place the capillary end in a container with the sample to be introduced, along with some way to inject the sample material into the capillary. After sample injection, the load end of the capillary is place again in the buffer, the driving electrical potential is established, and electrophoresis proceeds.

It is known to the present inventors to use a method of injection wherein the capillary at the load end is immersed in a sample volume, and the end opposite the loading end is sealed where it passes through a cap on a buffer solution reservoir. A relative vacuum is established in the space under the cap and over the buffer solution. Atmospheric pressure over the sample volume then injects sample into the capillary due to the pressure difference across the ends of the capillary. This procedure is a variation of hydrodynamic injection. It is also known to the inventors to use motor-driven apparatus to selectively immerse the capillary end in different sample volumes, by raising the capillary end, moving a stage supporting the buffer solution and a plurality of sample volumes, and lowering the capillary end in any of the samples. The same apparatus then raises the capillary end, moves the stage again, and lowers the capillary into the buffer solution containing the electrode again.

The apparatus described above is somewhat limited in the number of samples that may be accessed, and does not provide for sample injection by, or aided by, electromigration. Further, the apparatus described above limits the user to one buffer solution with an electrode.

In view of increasing demand for sample analysis, it is desirable to have an automatic apparatus that can be loaded with a relatively large number of samples, so a relatively large number of analytical procedures may be accomplished before manual intervention to maintain the system and to load additional samples for analysis. In the previous apparatus known to the inventors, it is conceivable to extend the stage to provide more positions for samples, but problems of sample deterioration such as by evaporation or thermal degradation, make that approach impractical. The more samples that are loaded, the more likely evaporation and thermal degradation is to be a problem.

What is needed is an apparatus that allows an electrical potential to be applied to sample volumes in their individual containers, so electromigration and electrokinetic injection may be used where desirable, either instead of or along with hydrodynamic injection. An improved apparatus also should provide a relatively large number of sample positions, so programming may be set to analyze a large number of samples between manual interventions. For such an apparatus to be practical, it must also provide for maintaining the viability of the samples yet to be analyzed, such as by addressing the problems of sample evaporation or thermal degradation.

SUMMARY OF THE INVENTION

An instrument is provided according to an embodiment of the present invention for performing capillary electrophoresis having an autosampler system for supporting containers of sample material to be electrophoresed and containers of buffer solutions, and presenting the containers to a load position.

The instrument also comprises a first electrode for providing a first terminus of an electrical potential to promote electrophoresis and a carrier configured to hold a first end of a capillary tube and the first electrode above the load position. The carrier is translatable for inserting the first end of the capillary tube and the first electrode into the containers presented to the load position by the autosampler system.

There is in the instrument in addition an outlet buffer reservoir for holding an outlet buffer solution for wetting a second end of the capillary tube and a second electrode positionable to contact buffer solution in the outlet buffer reservoir. The second electrode is for providing the second terminus of the electrical potential for promoting electrophoresis. A vacuum supply system is connected to the outlet buffer reservoir for creating a partial vacuum over the buffer solution in the reservoir.

A detector is placed between the ends of the capillary tube in one embodiment, and is operated to detect separated bands of samples passing along the tube. A microprocesser-based control system in another embodiment is employed to operate the instrument. Containers of samples and buffers used with the system are closed in one embodiment by a unique flexible septum with a duck-billed portion extending toward the container it closes, permitting easy entry of a capillary end and an electrode, while protecting the contents from contamination and evaporation.

In a preferred embodiment the autosampler comprises a rotary carousel with positions arranged in a circle for supporting containers. The carousel may be rotated to present individual containers to the load position. In another embodiment the carousel is translatable as well as rotatable, and has multiple circular locations for containers. A removable tray facilitates loading and unloading groups of sample containers and buffers to the instrument.

The instrument according to the invention provides a unique ability to run multiple samples for electrophoresis, and to select between hydrodynamic injection and electromigration, including electroendosmosis injection. Further, there are unique features for extending the utility of the present invention over the prior art. One of these features is the provision of flexible septa for closing containers, which acts to minimize contamination and evaporation over the relatively long periods of time required to perform multiple electrophoresis processes.

DESCRIPTION OF THE PREFERRED EMBODIMENTS

Figure 1:
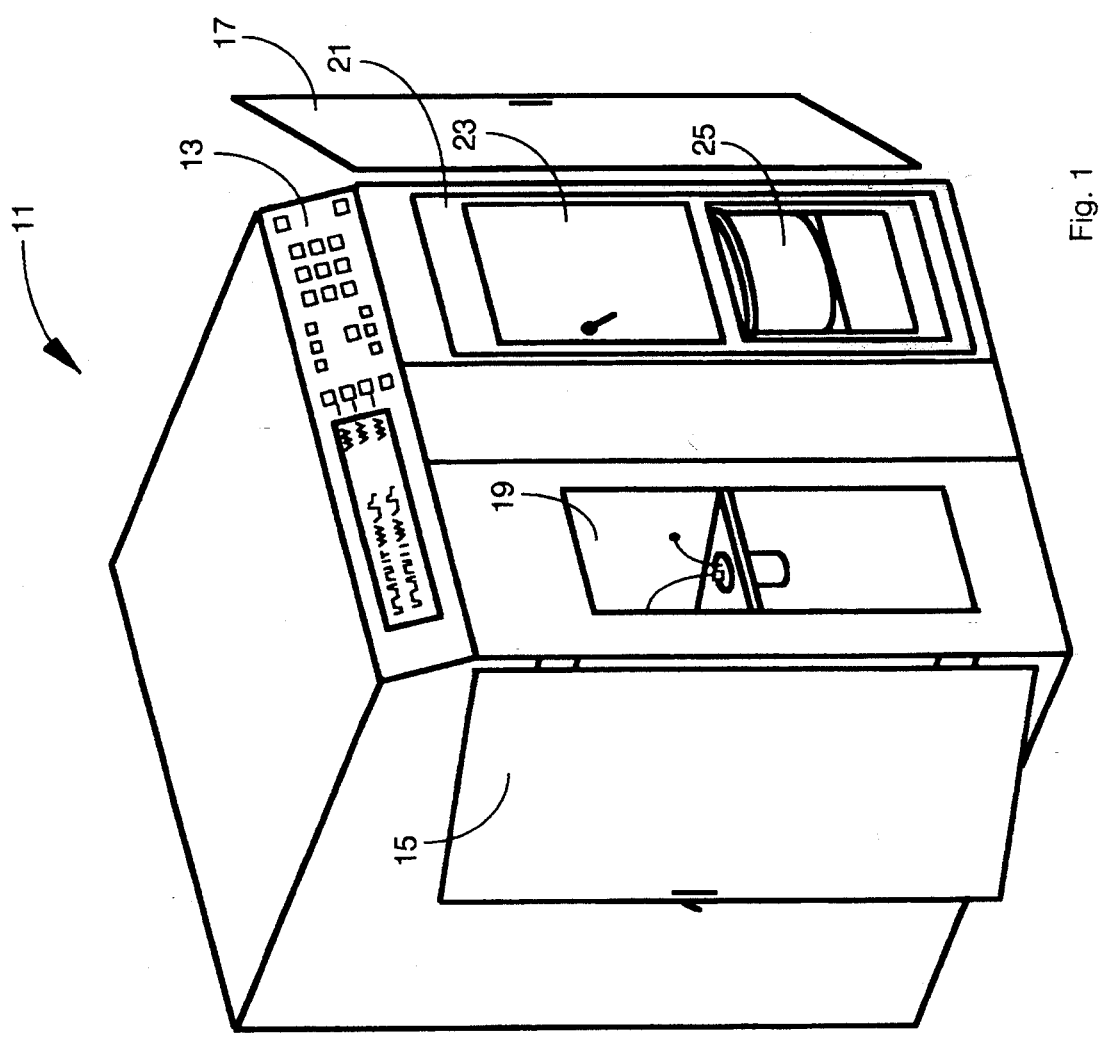
FIG. 1 is an isometric view of an instrument according to the invention.

FIG. 1 is a perspective view of an electrophoresis system 11 according to the present invention, which in the preferred embodiment is a Model 270A-HT system by Applied Biosystems, Inc. of Foster City, Calif. A control panel 13 occupies an upper portion of the front panel of the system, which has protective doors 15 and 17, shown open. The system comprises an outlet buffer electrode compartment 19 on one side and a thermostatted sample electrode compartment 21 on the other. The sample electrode compartment comprises a capillary oven (not shown) behind a door 23. The temperature of the interior of compartment 21 is controllable, including sensors (not shown) for sensing the temperature and communicating the temperature to a control system described below. There is also an extendable autosampler carousel 25, shown not extended.

Figure 2:
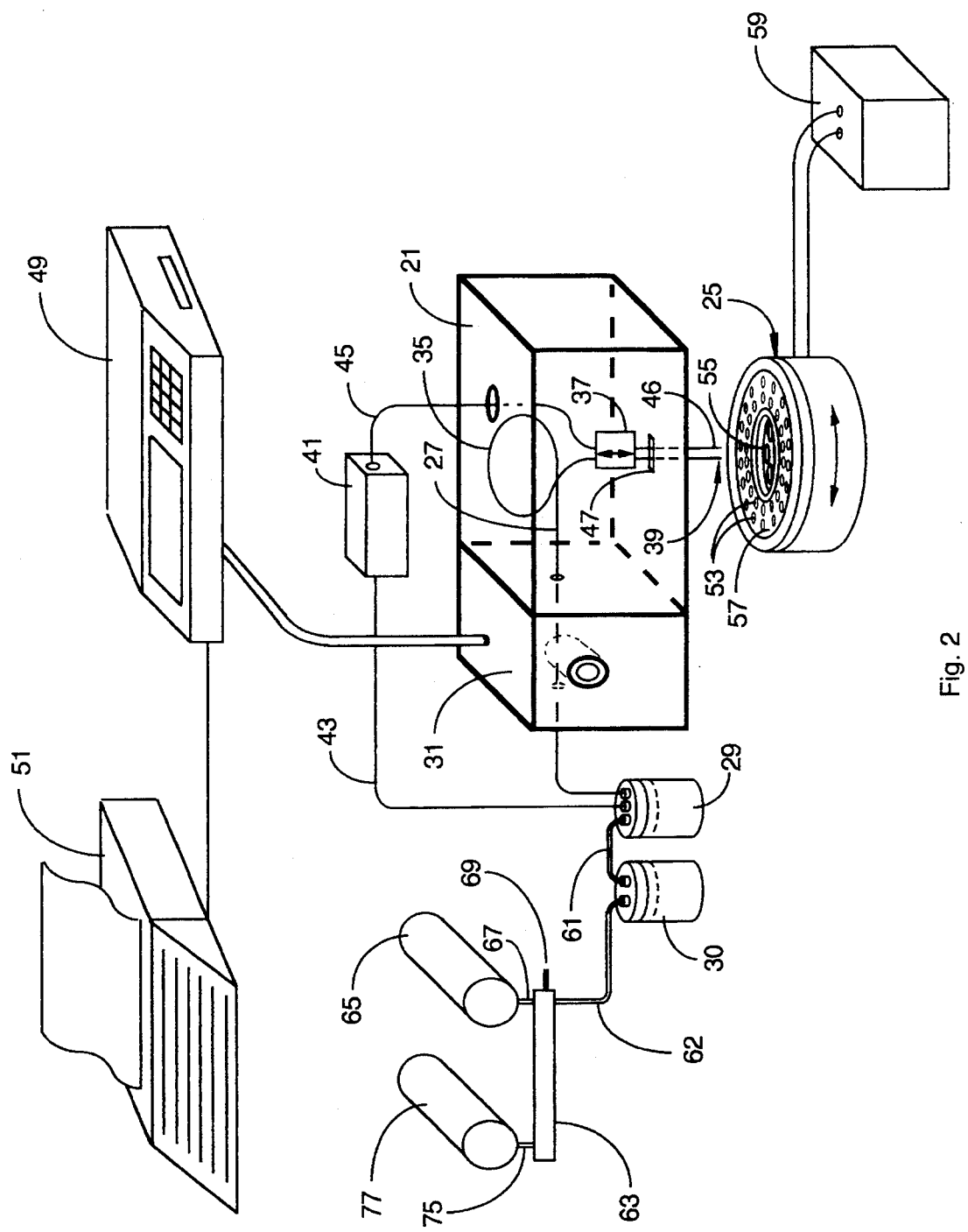
FIG. 2 is a largely schematic illustration of connection of elements of the invention.

FIG. 2 shows some principle elements of the system of the preferred embodiment in a schematic fashion separated from the supports and cabinet of FIG. 1. A capillary 27 passes on one end through a sealed lid into a vacuum buffer reservoir 29, and extends through a detector section 31 into thermostatted compartment 21. In thermostatted compartment 21 the capillary forms a loop 35 and is held by a movable carrier 37. An end 39 of the capillary extends below the carrier. The loop is made to accommodate the length of the capillary in the thermostatted compartment. The position of the carrier relative to the detector interface provides slack for manipulation, so end 39 can be raised and lowered into containers in the carousel without stressing the capillary.

Vacuum buffer reservoir 29 is connected by vacuum lines 61 and 62 through a sealed desiccant moisture trap 30 to a five position solenoid operated valve block 63. In one operating position, valve block 63 connects line 62 through the valve block to a low-vacuum reservoir 66 via line 67. Reservoir 65 is maintained at a vacuum level of about 5 inches of mercury. Valve block 63 in another operating position connects line 61, hence vacuum buffer reservoir 29, with a vent line 69. In this position the buffer reservoir may be vented to atmospheric pressure.

Valve block 63 provides connection also to a second vacuum reservoir 77 via line 75. Reservoir 77 is maintained by a vacuum pumping device (not shown) at a vacuum level of about 20 inches of mercury. The valve block may be positioned to connect vacuum reservoir 77 to buffer reservoir 29, and this mode is used to apply a differential pressure of 20 inches of mercury across the ends of capillary 27 typically to flush the capillary.

Reservoir 77 may be connected through valve block 63 to reservoir 65, and this position is used to maintain reservoir 65 at about 5 inches of mercury vacuum. The resolution of the vacuum control of reservoir 65 is dependent on the conductivity of the connecting lines and the time that the two reservoirs are connected. In the preferred embodiment the control is managed to maintain reservoir 65 at 4.95 inches of mercury vacuum, plus or minus 0.01 inches of mercury. The 4.95 inches of mercury vacuum level is used primarily for precise sample injections.

A variable-output power supply 41 provides driving potential for electrophoresis across the length of the capillary. One terminal of the power supply is connected by line 43 to an electrode sealed into vacuum buffer reservoir 29. The other terminal of the power supply is connected by line 45 to capillary actuator 37 where it connects to a platinum electrode 46 parallel to the capillary and ending substantially at end 39 of the capillary. From the actuator to end 39 the capillary and the platinum electrode are side-by-side, parallel, and both supported by actuator 37 in a manner that they may be extended through a slot 47 in the bottom of thermostatted chamber 21 and into containers on carousel.

Detector section 31 houses an optical detection system providing on-column UV absorbance detection, which is coupled to a microprocessor-based controller 49. Controller 49 is also coupled to sensor and drive components of the instrument to control instrument operations. A data reporting device 51, such as a strip-chart recorder, and a printer (not shown) are coupled to the controller to accept and record data, such as results of analyses, and diagnostic information.

Autosampler carousel 25 in a preferred embodiment carries fifty marker or sample vials in registers in two outer circular rows 53 and eight larger buffer vials in registers in an inner circular row 55. The vials are supported in an inner tray 57 that may be lifted out of autosampler carousel 25 when the carousel is extended from the cabinet of the machine.

For situations where it is desirable to maintain samples and buffer solutions at a temperature other than ambient, there is a heater/cooler 59 for circulating refrigerated and/or heated liquid through channels (not shown) internal to carousel 25. Because buffers have been found to perform better at near ambient temperature, the temperature changing coils in the carousel have been provided preferentially in the region of sample vials. The central region used for buffer vials is insulated from the heating and cooling apparatus.

Figure 3:
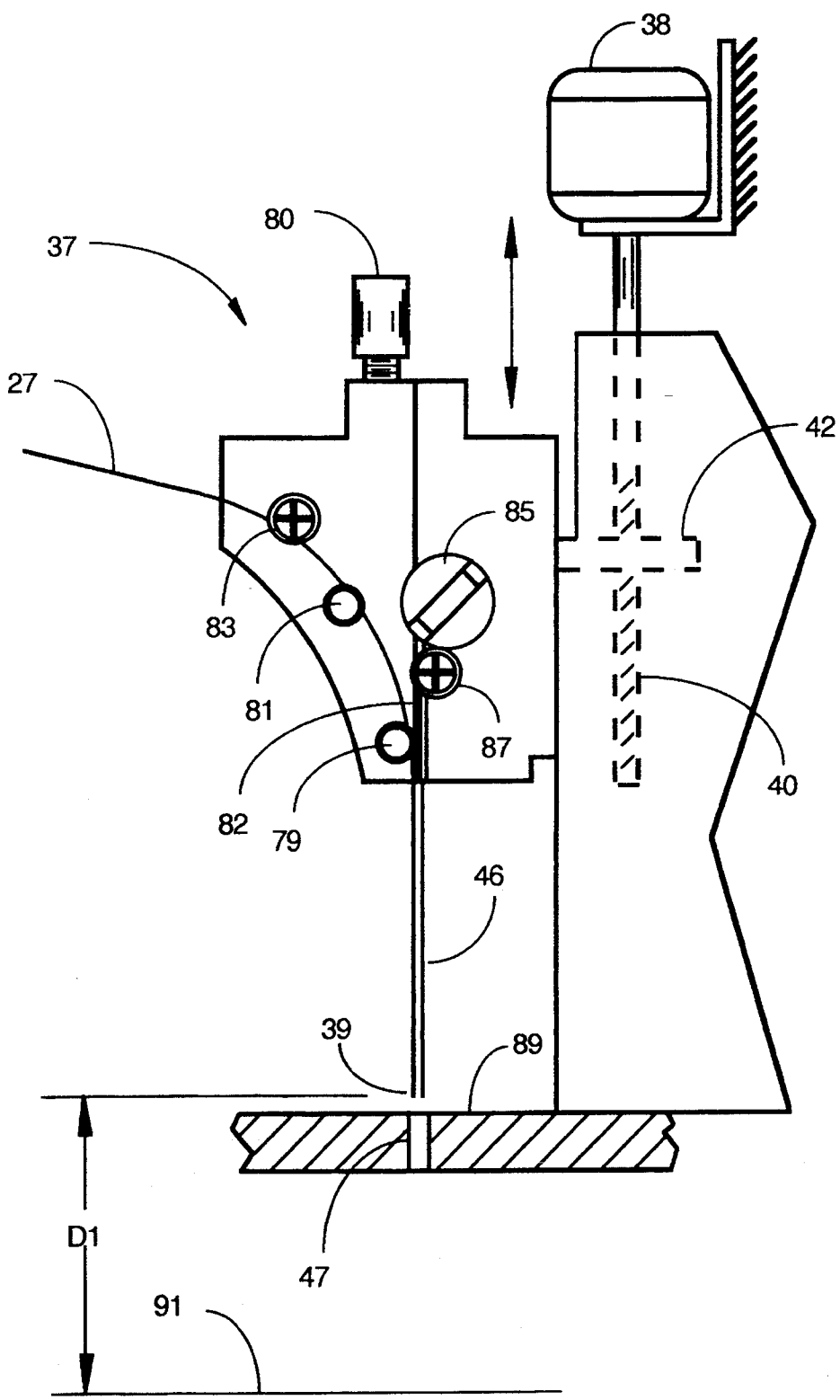
FIG. 3 is an elevation view of a carrier for vertical translation of an electrode and a capillary in the invention.

FIG. 3 is an elevation view of actuator 37 showing additional detail. Actuator 37 is moved vertically by a drive mechanism including a stepper motor 38 and a threaded shaft 40 engaging a matching thread in an arm 42 attached to carrier 37. The threaded shaft has a long pitch, about 0.5 cm. in the preferred embodiment, so a single revolution of the motor results in a relatively long vertical displacement of the carrier. The long pitch allows rapid vertical actuation of the capillary and electrode. When it is time to change the electrode or to install a new capillary, with power off to the stepper motor, the pitch of the driver screw is long enough that one may lift or lower carrier 37 with knob 85, (which is also used to clamp the electrode in place) rotating the motor shaft, and the carrier stays in place when the knob is released.

As described above, line 45 (FIG. 2) connects one terminal of the power supply to carrier 37 and to a spring loaded contact within the carrier such that platinum electrode 46 inserted in an opening in the bottom of carrier 37 makes electrical contact. Other components of the carrier are insulated from the high voltage electrode. Retainer knob 85 holds the electrode against the contact within the carrier and guide screw 87 helps to align the electrode vertically. The position of the electrode may be extended or retracted within limits, and the lower end position may also be controlled by substituting electrodes of different lengths in the carrier.

Capillary 27 passes under a retainer screw 83, a clamp screw 81, and an alignment screw 79, and bears against a substantially vertical shoulder 82. Alignment screw 79 has a conical shaft, so turning the alignment screw Clockwise moves the capillary toward shoulder 82, and counterclockwise allows the capillary to move away from the shoulder. Once the capillary is adjusted parallel to the electrode, lock screw 80 may be tightened to lock the alignment screw in place.

In the uppermost position shown in FIG. 3, the capillary tip and electrode tip are about 1.6 mm. (1/16 inch) above lower surface 89 of the sample electrode compartment. In the lowermost position, indicated by line 91, after stroke D1, the electrode and capillary tip are at an elevation providing full insertion into vials in the autosampler carousel.

Figure 4:
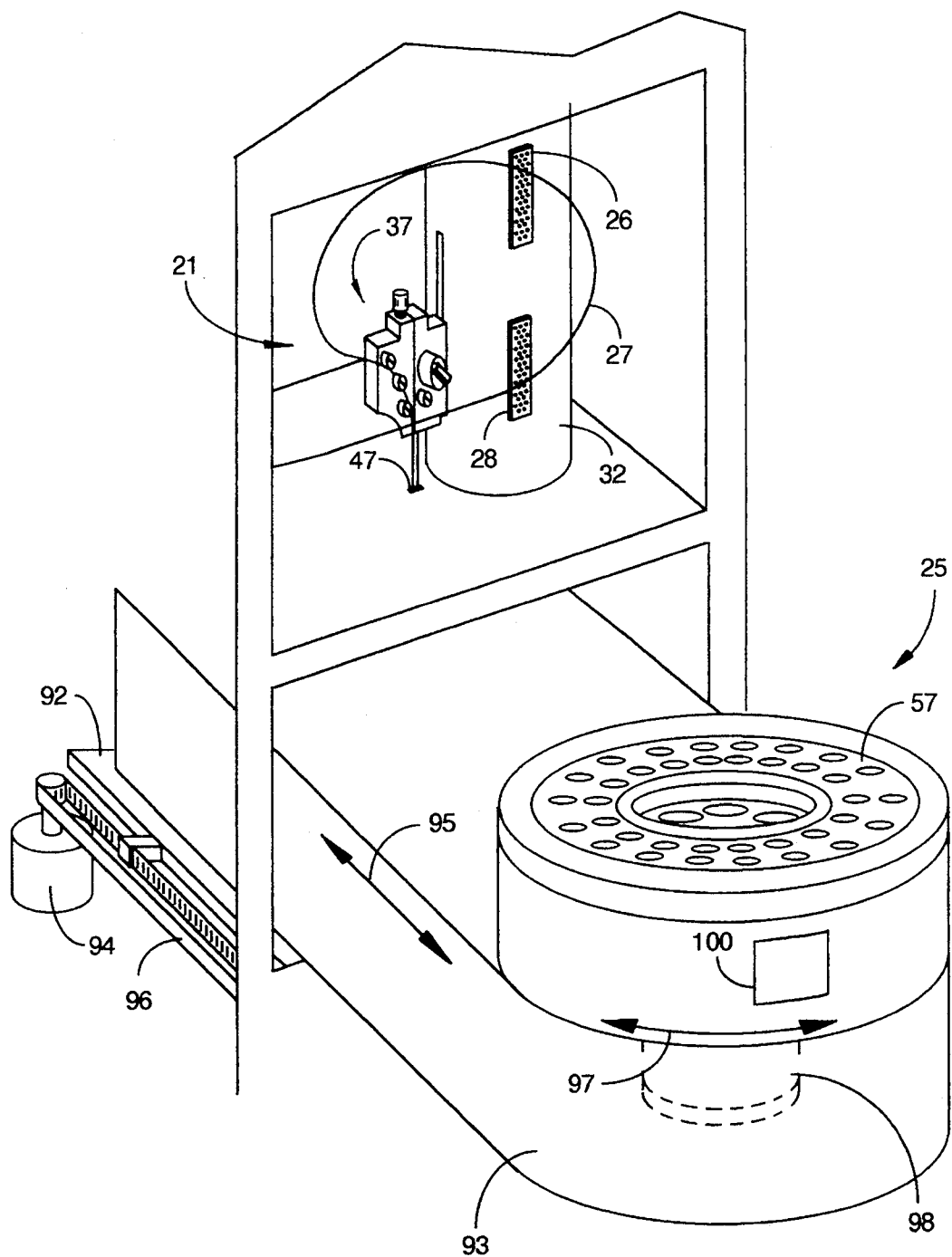
FIG. 4 is an isometric view of an autosampler carousel according to the invention for presenting samples and buffers to the capillary.

FIG. 4 is an isometric view of carousel 25 and sample electrode compartment 211 above the carousel. The carousel is shown extended. The carousel is supported on a shelf 93 that is in turn supported on a conventional double slider ball bearing mechanism 92, driven in the direction of arrow 95 by a stepper-motor 94 driving a gear belt mechanism having a gear belt 98 attached to bearing mechanism 92. The carousel is rotated (arrow 97) by a stepper motor 93 driving a gear mechanism (not shown). The drive for extending shelf 93 is used to extend the carousel so trays 57 of sample vials and other containers may be exchanged. By extending the carousel one may also replace individual ones of the vials the inner tray may support. The drive is also used in conjunction with rotating the carousel to position all vials directly below and in line with the side-by-side electrode 48 and capillary 39 (FIG. 3). A window 100, of plexiglass in the present embodiment, is provided in the rotary portion of the carousel to allow an operator to view the vials in the carousel from below.

For positioning vials for insertion by the electrode tip and capillary end, there are position sensors (not shown) associated with the extendable shelf so the shelf may be stopped at four distinct positions of extension. One position places the outer circumferential row of 25 sample vials in line with opening 47 so each of the 25 vials may be placed below the opening by rotating to each of the 25 radial positions. Another extension position of the tray aligns the second row of 25 sample vial positions with the opening. A third extension position aligns the circumferential row of 8 buffer vial with the opening, and the fourth position is the fully extended position used for changing the tray. The first three positions leave the carousel behind door 17 (FIG. 1), and these three are operational positions used with the system at high voltage.

In the sensing apparatus and circuitry for positioning shelf 93 there is one additional position to the four positions described above. This is a home position sensed and used as a starting point for driving to other positions. The sensors in the preferred embodiment are infrared diode and receiver pairs, and positions are sensed by "flags" that extend between a diode and receiver at particular positions in translation of shelf 93.

The control routines for the system are written so the home position is sought whenever there is a definable uncertainty as to where the tray is in the in/out position. For example, since the drive is by stepper motor, it is quite possible for a user to physically move the tray, rotating the stepper motor without a drive signal, which causes the control to lose track of position. In such a case, the system seeks the home position before seeking any of the other four positions.

Capillary 27 is shown in FIG. 4 assembled to carrier 37. The capillary is looped in this embodiment once in the compartment, and held in position my impressing it into two Velcro TM pads 26 and 28 that are typically fastened to column The Velcro TM pads provide a convenient mounting, providing flexibility for vertical movement of carrier 27, and also hold the capillary away from grounded components, where a high-voltage arc might jump from the electrode to the component.

Figure 5:
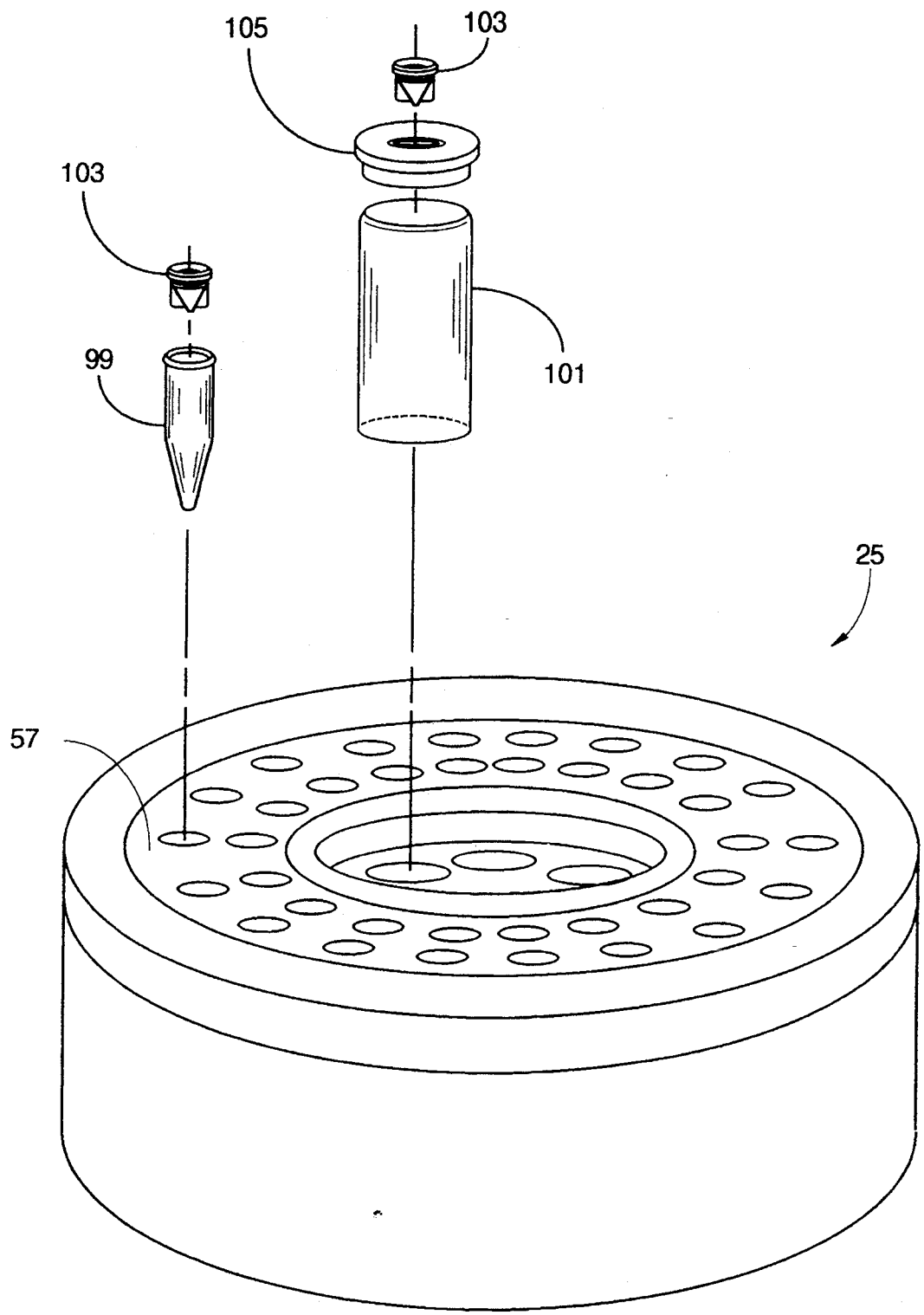
FIG. 5 is an enlarged view of the carousel of FIG. 4 showing a sample vial and a buffer vial.

FIG. 5 is an isometric view of the carousel with a sample vial 99 and a buffer vial 101 shown in exploded view above the carousel. Vials are not shown in FIG. 4 to avoid excessive and possibly confusing detail. A flexible slitted septum 103 closes the top of sample vials and buffer vials to prevent spillage and especially to prevent evaporation without impeding the entry and withdrawal of the electrode tip and capillary end. The septum also wipes the capillary and electrode when these are withdrawn from a sample or a solution, and helps thereby to prevent or minimize carryover. The septum has a duck-billed portion extending toward the vial for easy entry while still providing positive closure. To be able to use the same septum on the buffer vials, which have a larger diameter than the sample vials, a septum adapter cap 105 is used between the vial and the septum.

The removable nature of tray 57 allows a worker to prepare samples off line, load the samples to vials, to prepare buffer solutions, and then to extend the carousel, remove the tray, and replace used sample and buffer vials with a whole new set for a new series of runs.

Figure 6A:
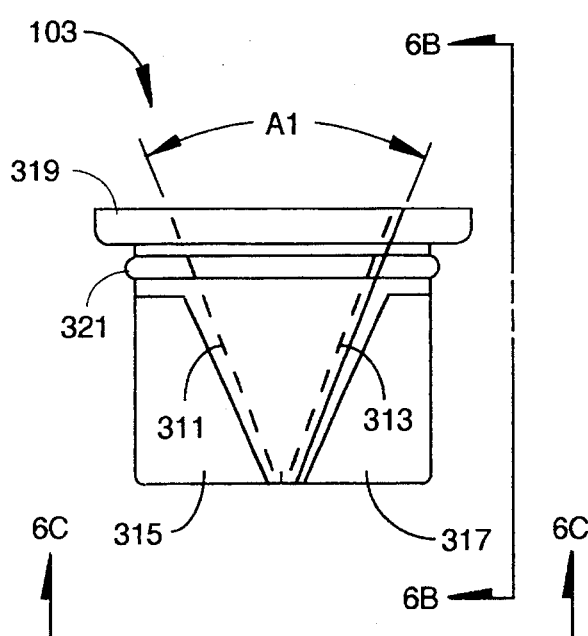
FIG. 6A is an elevation view of a septum according to the invention for closing sample and buffer vials while allowing entry of a capillary and an electrode.
Figure 6B:
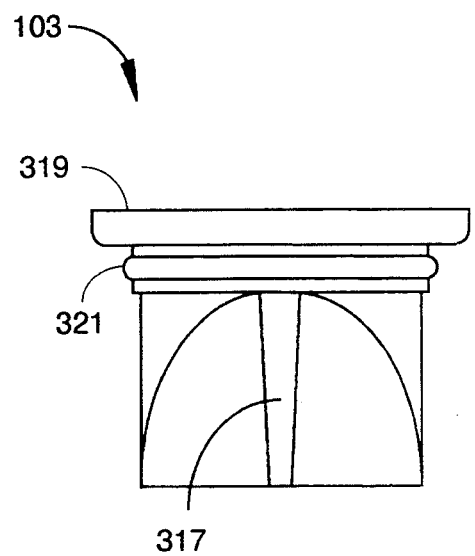
FIG. 6B is an elevation view of the septum of FIG. 6A rotated 90 degrees.
Figure 6D:
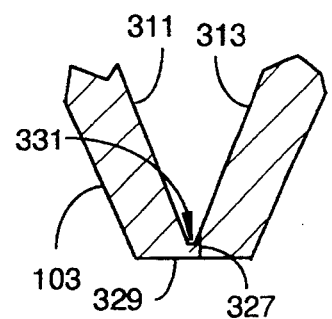
FIG. 6D is a section view of a portion of the septum to illustrate a problem that can occur in cutting a slit in the septum.
Figure 6C:
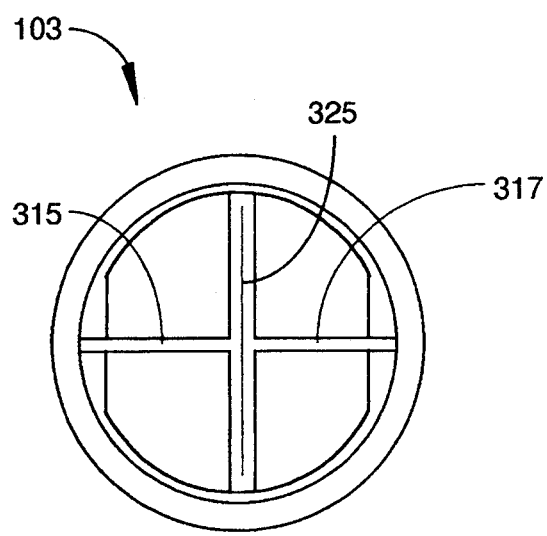
FIG. 6C is an end view of the septum of FIG. 6A.

FIGS. 6A, 6B, and 6C are orthogonal projection views of septum 103. FIG. 6B is an elevation view of FIG. 6A in the direction of view line 6A—6A of FIG. 6A. FIG. 6C is a "bottom" view in the direction of view line 6C—6C of FIG. 6A.

FIG. 6A shows, among other things, the shape of the duck-billed portion described above which extends toward a container closed by the septum. Inside surfaces 311 and 313 shown by dotted lines are the inside of opposing walls angled inward, define an included angle A1 in this embodiment of about 44 degrees, and form guiding planes for the approaching electrode and capillary end in operation.

Elements 315 and 317 are molded "wings" with a function of providing support to the walls of the inwardly sloping surfaces. An upper rim 319 positions the septum against the top rim of a container when the septum is inserted into the container, and a molded ring 321 provides positive closure into a groove in the top of a vial closed by a septum. Groove 323 (FIGS. 6F and 6G) is exemplary.

Bottom view FIG. 6C shows a slit 325 through the septum generally along the line of intersection of the sloping walls that define the duck-billed portion of the septum. The slit is made by a sharp instrument, and is preferably made from the "inside". That is, a blade is inserted into the septum following the inward sloping walls of the wedge-shaped opening until the blade is at the bottom of the opening, then the blade is urged through the material to make the slit. If the cut is made from the other side, that is, the side that is meant to be on the inside of the container, the opening into the inner duck-billed portion is often not at the bottom of the wedge-shaped opening, but some distance up one of the sloping walls.

FIG. 8D is a magnified section taken at the "bottom" of the septum and shows a typical result of making the slit from the "below" that is, beginning on surface 329. The problem is that surface 329 has a width of from about 0.7 mm to about 1 mm in the preferred embodiment, and the septum is a of a flexible material, in the preferred embodiment Chloro-butyl compound No. 910-40, available from Gardena Rubber Co., Inc. The preferred durometer is about Shore A40.

If the slit is not started at the center of surface 329, it may pierce the opposite side through one of the walls, as slit 327 in FIG. 8D pierces wall 313, creating a pocket 331. This pocket is a trap such that, if the capillary or electrode contacts and follows down the sidewall of the septum (311 of FIG. 8D) as carrier 37 (FIG. 4) is lowered, it will be caught in the pocket. Further lowering of carrier 37 can break the capillary or pierce the septum with the electrode.

Figure 6E:
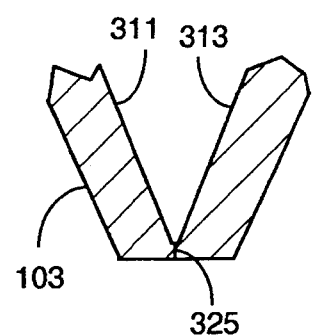
FIG. 6E is a section similar to FIG. 6D showing correct placement of a slit in the septum in the invention.

FIG. 6E shows slit 325 in the septum of the present invention, having been made from the "inside", and avoiding the formation of a pocket.

The septum of the present invention has an overall diameter of about 10 mm, and an overall height of about 7.5 mm. The sloping sidewalls, as described above, define an included angle of about 44 degrees. Slit 325 is about 8.5 mm in length along surface 329.

Figure 6F:
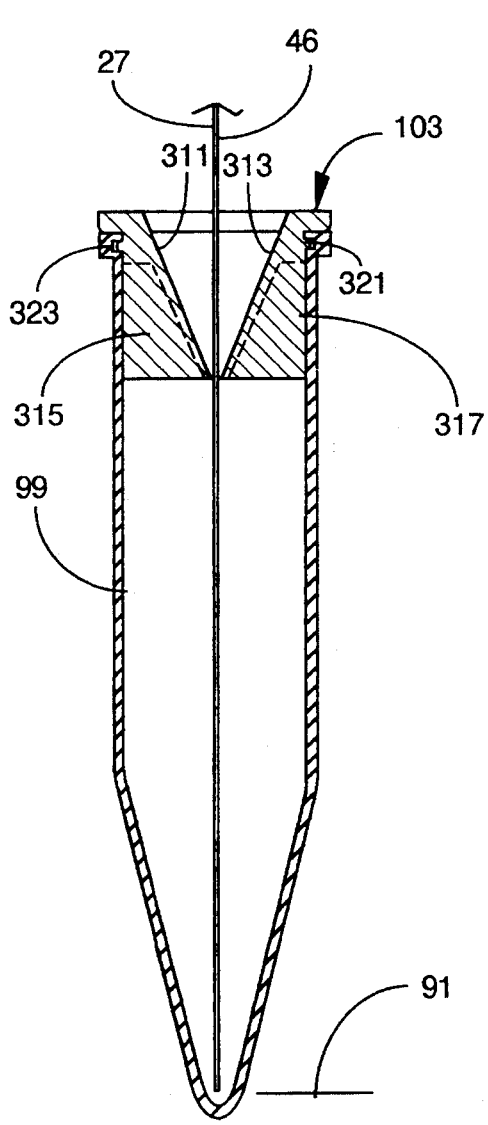
FIG. 6F is an elevation section view of a sample vial and a septum assembled according to the invention.

FIG. 6F is an elevation section view of a sample vial 99 with septum 103 in place and electrode 48 and capillary 27 inserted to position 91 (shown also in FIG. 3), at which position the electrode and capillary are fully inserted. In FIG. 6F, to best illustrate the nature of the duck-billed portion of the septum, the section is taken in the direction across the wide part of the duck-bill, so the electrode is hidden behind the capillary, and both do not show.

Figure 6G:
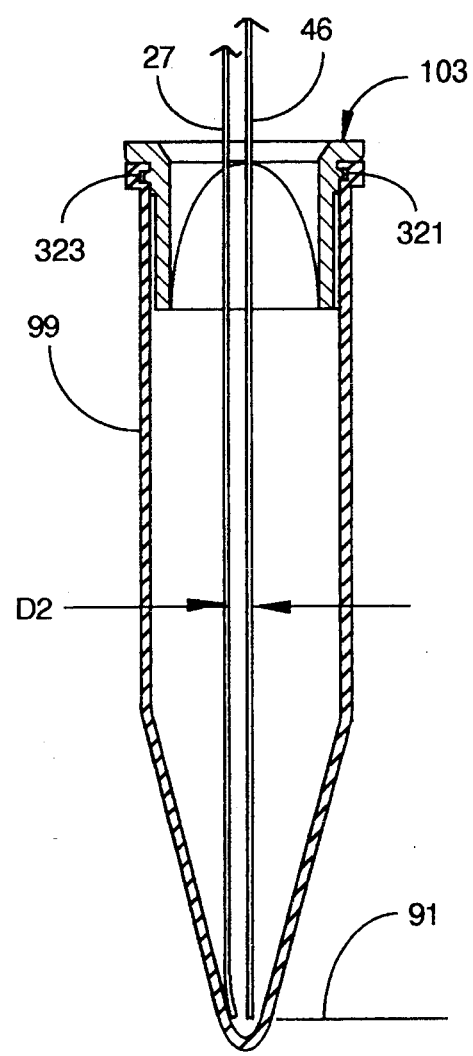
FIG. 6G is an elevation section similar to FIG. 6F rotated 90 degrees.

FIG. 6G is a section of sample vial 99 as in FIG. 6F, but rotated 90 degrees from the view of FIG. 6F to show the duck-billed portion with electrode 46 and capillary 27 side-by-side. In FIG. 6F and FIG. 6G molded ring 321 is shown engaged in groove 323 of vial 99.

The electrode tip is a relatively rigid element, and not given to easy flexure. The capillary, on the other hand, is a relatively thin and flexible element. For this reason, if carrier 37 is lowered and the electrode does not enter the slit straight on, but encounters one of the sloping sidewalls instead, the electrode will tend to cause the vial to move in the tray until the slit is entered. On the other hand, the capillary will flex more readily. For this reason, the capillary is shown somewhat deflected in FIG. 6G.

Dimension D2 between the capillary and the electrode varies somewhat in the embodiment described herein, and is typically about 3 mm. For the two to enter a vial side-by-side the entry slit should be at least as long as the distance D2. In the present embodiment of the invention the slit is about 6.5 mm in length. The slit, however is not always aligned with the plane defined by the electrode and capillary, and one or both often encounter one of the sloped walls of the septum as entry is accomplished. Accordingly the septum is treated with a friction-reducing agent to facilitate relative movement between impinging tips and the walls of the septum. A suitable treatment is with silicone oil, which forms a low friction interface for the electrode and the capillary, and prevents seizure and grabbing as the electrode and capillary are inserted. There are other materials that might be used for the purpose, and other treatments than the one described below, for treating the septa to reduce sliding friction.

In the present embodiment the treatment of the septum proceeds as follows:

Firstly a batch of septa, typically 10,000 at a time, are washed in a solution of dodecyl sulfate and sodium salt (SDS), and deionized water, after which they are rinsed several times in deionized water.

Secondly, the batch of septa is immersed in a 2% solution of Dow Corning #36 Silicone Emulsion and stirred for several minutes.

Thirdly, the septa are dried in an oven at about 50 degrees C. for a period of time up to about 12 hours.

Another problem that has been found to be common to operation of the apparatus described is carryout of buffer solution when withdrawing a capillary from a buffer vial through the slit in a septum. Carryout has been found to be closely related to the linear rate that a capillary is withdrawn. For example, when a 375 micron diameter capillary is withdrawn at a rate of about 25 mm (1 inch) per second from a buffer vial with citrate buffer, droplets of from 1 to 3 micro-liter volume appear to adhere to the capillary.

Experiments have determined that to avoid carry-over problems, the withdrawal rate should not exceed about 20 mm. per second, and to provide a factor of safety, more preferably about 13 mm. (0.5 inch) per second. Accordingly, the drive controls have been designed so that the vertical (z-direction) drive is maintained at about 13 mm. per second for capillary withdrawal.

Figure 6H:
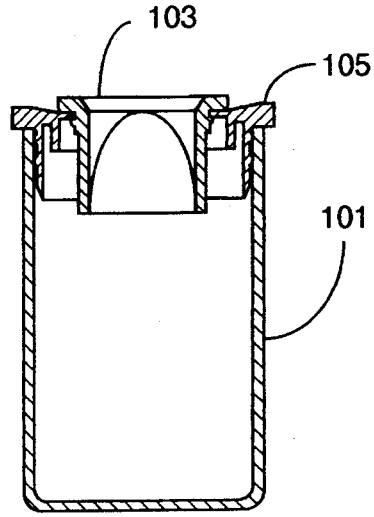
FIG. 6H is an elevation section view of a buffer vial with a cap and a septum according to the invention.

FIG. 6H is a section of buffer vial 101 with an adapter 105 and a septum 103 in place. The adapter presents a rim similar to a sample vial for the septum. The adapter is molded from relatively inert plastic material, and allows the septum used for the sample vials to also be used with buffer vials.

Figure 7:
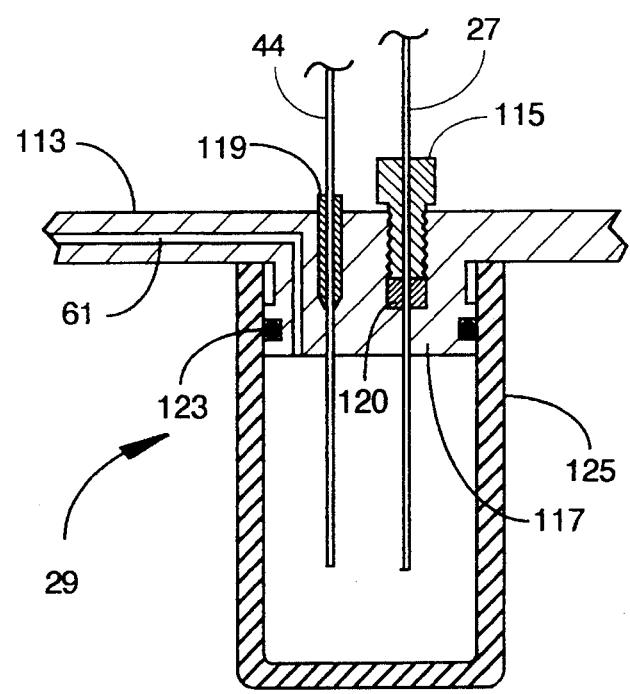
FIG. 7 is an elevation section view of a vacuum buffer reservoir according to the invention.

FIG. 7 is an elevation section view of vacuum buffer reservoir 29 located in outlet buffer electrode compartment 19 (FIG. 1). The vacuum buffer reservoir provides buffer immersion for the capillary end and electrical potential from the power supply at the end of the capillary opposite end 39 where sample is introduced. Electrophoresis requires an electrical potential from one end to the other of the capillary to provide the electrical driving force.

Buffer reservoir 29 is shown in FIG. 2 in a way that is largely symbolic. The vacuum that may be applied above the buffer in the buffer reservoir from vacuum reservoirs 77 and 66 also provides for hydrodynamic sample injection at the sample end of the capillary.

In the embodiment described, reservoir 29 comprises a circular projection 117 from a plastic shelf 113 and a plastic bottle 125 that mounts over the projection sealed by an o-ring 123. The shelf also includes mounting for desiccant moisture trap 30, not shown in FIG. 7. Vacuum line 81 between the desiccant trap and the vacuum buffer reservoir, shown as a separate line in FIG. 2, is actually a passage within shelf 113 as shown in FIG. 7.

Electrode 44 extends through an insulating and sealing insert 119 and connects to line 43 from the power supply (FIG. 2). Passage 61 opens through projection 117 of shelf 113 into the interior of bottle 125. Capillary 27 extends through a sealing septum 120 to a point near the bottom of the outlet buffer reservoir, and the septum is held in place and compressed by a plastic threaded fastener 115.

To empty, clean, or fill the outlet buffer reservoir, it is necessary to vent the space above the buffer in the reservoir to atmospheric pressure by actuating valve block 63. Vessel 125 then may be pulled downward and removed.

Desiccant moisture trap 30 (FIG. 2) is built into shelf 113 much as is the outlet buffer reservoir, and has an o-ring seal. Desiccant material to prevent moisture from being drawn into the vacuum system is placed in the trap as needed.

Process Related Functions

Specifics of the apparatus according to an embodiment of the invention are described in substantial detail above. Operation, including the nature of control routines and an operator interface, are described below. Certain functionality is described in the present section related to the apparatus described above.

It has been described that sample material may be injected by electrokinetic operation and by hydrodynamic operation. With the unique apparatus of the invention injection may be accomplished by both techniques and the relative contribution of each technique may be controlled. Moreover, the relative vacuum and the electrical potential may be varied during a sample run to accomplish a number of desirable results.

The operation of the apparatus has been described thus far with particular emphasis on injection of samples into a capillary at the carousel end, and electrophoresis through the system to buffer reservoir 29. In many instances in operation samples are passed into the buffer reservoir and discarded. This is not, however, a required mode of operation. The unique combination of elements provided in accordance with the present invention allows electrophoresed samples to be reversed in a capillary and carried back to the carousel, where individual samples may be deposited in sample vials for removal and later quantification and other analysis. To accomplish this purpose, a pressurized gas supply, typically Nitrogen or other relatively inert gas, is connected to buffer reservoir 29 through a solenoid operated valve, and the buffer reservoir may be pressurized to a controlled extent to expel material from a capillary.

In one embodiment of the invention a switchable power supply is used with a capacity of 30,000 volts, with one terminal grounded and the other switchable from positive to negative relative to the grounded terminal, so opposite voltages may be conveniently switched to the apparatus.

Yet another feature of the present invention is related to the nature of capillaries used in the apparatus described. In some instances capillaries are used with a "clean" bore; that is, without a gel. In other instances gel-filled capillaries are used. In the procedures using gel-filled capillaries, the capillaries are typically provided with some protection, like a protective removable tip that may be removed at the time the capillary is put into service.

It has been found by experience that delays, such as when changing a carousel, can be detrimental to a gel-filled capillary, in that the gel at the end of the capillary "dries out" and does not operate properly when re-immersed. To alleviate this condition, one buffer vial is provided on the carousel with a protective material, and the gel-filled capillary is dipped into this material before the tray is changed on the carousel. The protective coating on the capillary end prevents drying of the gel until the capillary is immersed in a cleaning material after operation re-commences.

The operational software has a procedure wherein the operator specifies the nature of the capillary, and if the capillary is gel-filled, the operational routines will include this protective step. In a preferred embodiment the protective material is ethylene glycol and the cleaning material is deionized water. Glycol, polyethylene glycol, and other water soluble polymers may also be used as the protective material, each having a lower volatility than water, and removable with water.

Operation

Capillary electrophoresis has a number of advantages for particular sets of circumstances in electrophoresis, among them that very small samples may be employed. Another advantage is that higher voltages may be used, which generally translates to faster run times than for other electrophoresis techniques. The bore of the capillary is typically in the range of 50 to 100 micrometers, and the small bore diameter translates to a large surface-to-volume ratio. This allows efficient dissipation of heat from the current passing through the capillary, and makes "free solution" electrophoresis practical; which is electrophoresis without a gel.

Capillary electrophoresis is well suited for automation partly because it allows for on-line detection and automatic sample introduction. By detecting bands in the capillary by absorbance many conventional electrophoresis steps, such as gel staining and destaining, are eliminated. Samples may be drawn into the end of the capillary in nanoliter aliquots from microliter samples in vials.

There are four principle modes of separation that may be accomplished with the capillary system of the invention. These are size-exclusion gel electrophoresis, Isoelectric Focusing (IEF), Free Solution (also known as Capillary Electrophoresis, or (FSCE), and Micellar Electrokinetic Capillary Chromatography (MECC). Of these, gel electrophoresis and IEF are extensions of conventional practice to capillaries. FSCE and MECC are unique to capillary electrophoresis.

Both FSCE and MECC are performed in solution without a gel matrix. FSCE relies on separation by differences in mobility dependent typically on charge and size of analyte species. MECC is a chromatographic method taking advantage of analyte partitioning between aqueous and micellar phases.

Figure 8:
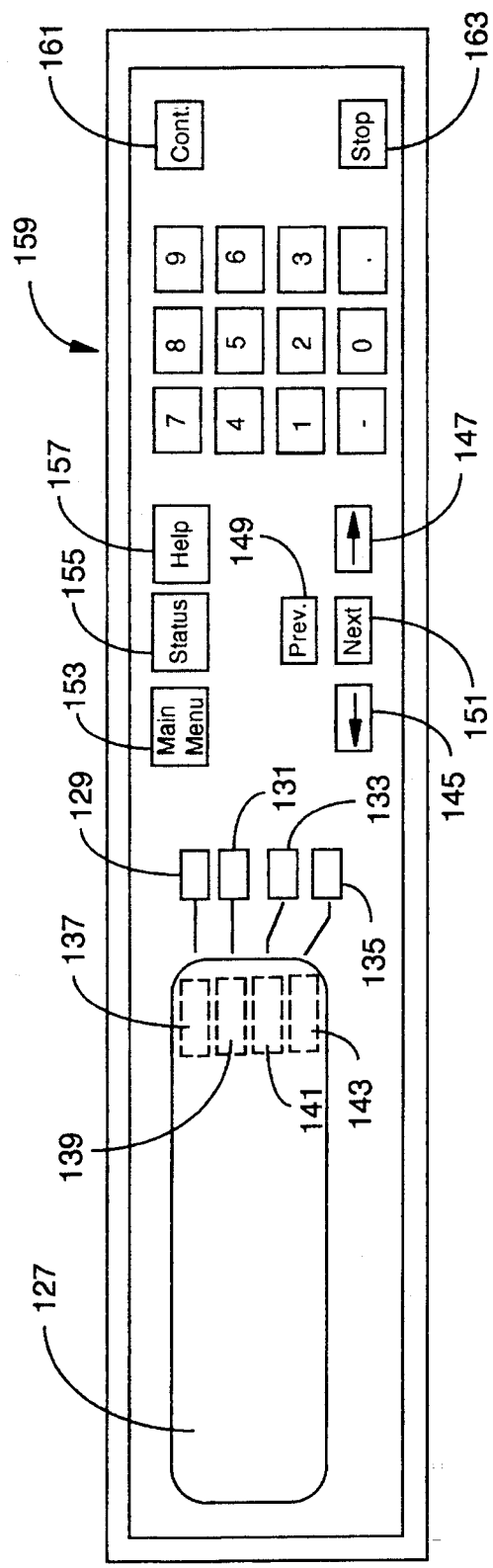
FIG. 8 is a layout of a control panel for the instrument shown in FIG. 1.

FIG. 8 is a view of control panel 13 in more detail than shown in FIG. 1. A 4 line by 40 character display screen 127 displays menus for the operator to select functions and status information for the operator. There are four "soft" keys 129, 131, 133, and 135 in a vertical row to the right of the display screen, each associated with a display area on the screen. Key 129 with area 137, key 131 with area 139, key 133 with area 141, and key 135 with area 143. Options are at times presented in the display areas, and options may be selected by the operator by pressing the associated soft key.

In addition to the display areas associated with soft keys, the screen also displays in conjunction with menus, interactive fields which the operator may use to enter system parameters or to select parameters from pre-stored values. Fields are typically displayed as rectangles on the screen. Only one field at a time is active, and the active field is indicated by a blinking rectangle. Arrow keys 145 AND 147 are used to step through the fields in a display, making different fields active one-at-a-time for input. Where a field has a selection of allowed values, the Prev. key 149 and the Next key 151 are used for indexing through the list of allowed values, each of which is displayed in the field.

There are three "immediate" keys 153, 155 and 157 which activate immediate functions. Main Menu key 153 cycles the display immediately to a Main (top level) Menu described further below. Status Key 155 causes the system to display the current instrument conditions or run status information, if a run is in progress. Help Key 157 provides a brief explanation of options available from the current menu.

An array 159 of number keys including a "minus" and a "decimal point" are for entering numerical values into certain fields that will accept numbers when active. The number keys are inactive unless a field is active that will accept numbers.

Finally there are two control keys 161 and 163 to the right side of the control panel. The Cont. (for continue) Key 161 is for continuing a run that has been interrupted by pressing a soft key marked Pause, which temporarily interrupts a run sequence. The Stop Key 163 is for immediately stopping any run that is in progress. A run that is stopped by the Stop Key can only be restarted from the beginning. It cannot be continued.

The instrument operates by executing a series of cycles. Each cycle is a pre-defined and named set of actions for which the operator may customize operating parameters. Setting parameters or programming a method is done in the process of editing a method, described below. A Method is a series of cycles terminating with the End Cycle described immediately below. Through use of menus the operator may define as many as 10 User Methods, each of which may include up to nine cycles. A sequence is a series of methods which an operator may define by editing tools, the sequence to be carried out by the instrument automatically without further intervention.

The cycles are:
1. Detector Cycle—Autozeros the detector and sets the various conditions for UV absorbance detection for a run. Parameters to be set are wavelength, absorbance range, rise-time, and autozero (yes or no).
2. Flush Cycle—Used to flush the capillary to remove any traces of old sample or contamination, and to equilibrate the capillary with the run buffer. Flushing may be by vacuum (pressure differential) or electroendosmotic pumping, using electrical potential across the ends of the capillary with buffer. Parameters to be set are flush time, oven temperature, vial position for the autosampler (1–58), voltage and polarity, vacuum level, detector wavelength, and use of a buffer incrementing method. The incrementing method moves the inlet capillary end to the next buffer vial in sequence at specified intervals. A purpose of the buffer incrementing method is to prevent buffer ion depletion when carrying out automated multiple analyses.

3. Marker Cycle—Injects a neutral standard marker or internal standard from a sample vial (typically) into the capillary. Parameters are injection time, oven temperature, marker vial position, voltage and polarity, vacuum level, and detector wavelength.

4. Sample Cycle—Injects an aliquot of a sample into the capillary. Samples may be injected by pressure differential or by electromigration. Parameters are injection time, oven temperature, voltage and polarity, vacuum level, and detector wavelength.

5. Time Cycle—Applies a selected voltage to move a sample electrophoretically (causing separation) through the capillary and monitors migration at a selected wavelength. Parameters are time, buffer vial to be used, voltage and polarity, vacuum level, oven temperature, and detector wavelength.

6. End Cycle—This cycle is to designate the end of a series of cycles that define a Method. There are no parameters.

Figure 9:
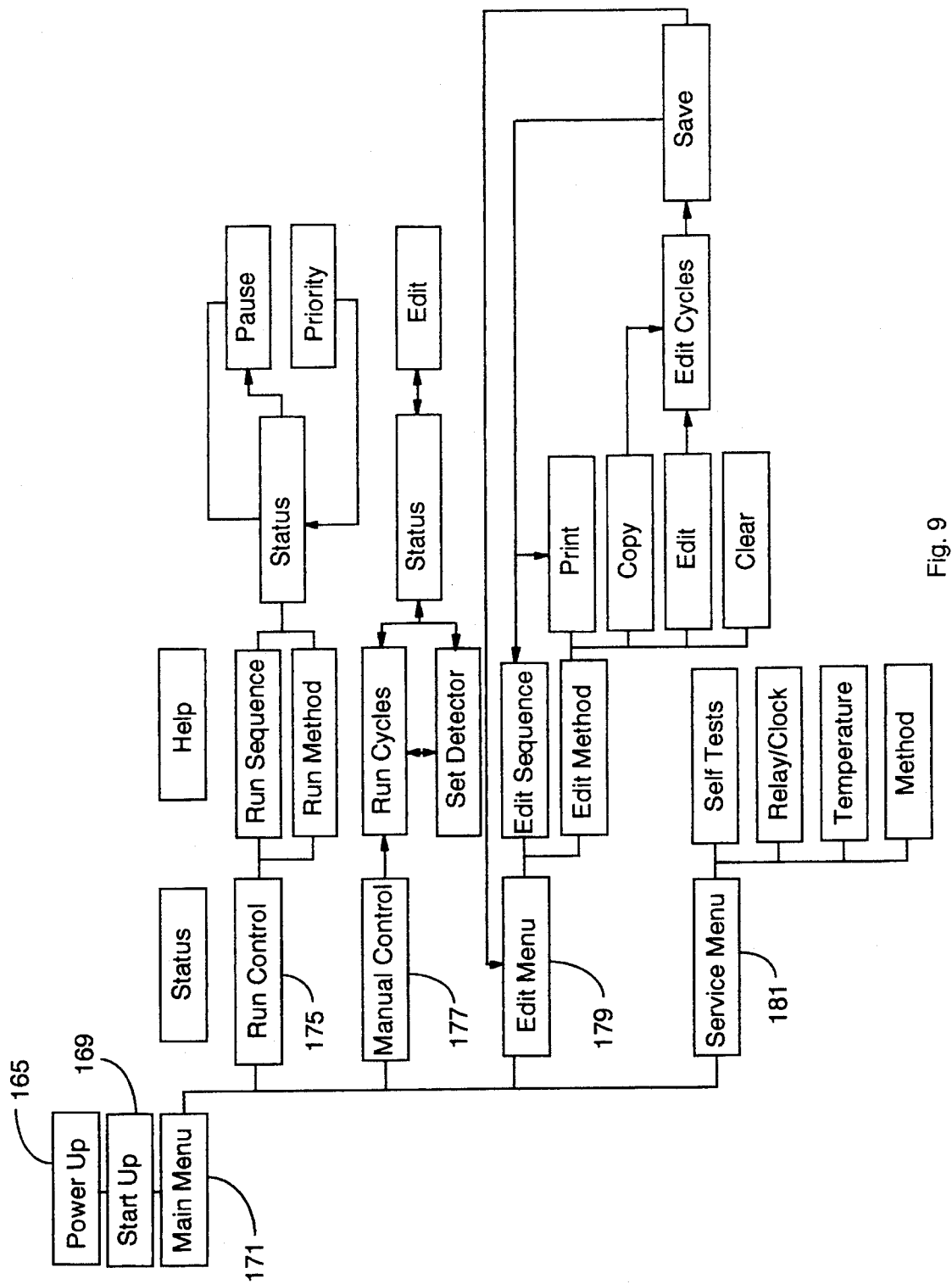
FIG. 9 is a diagram of pre-stored menus and information displays for the instrument of the invention.
Figure 10:
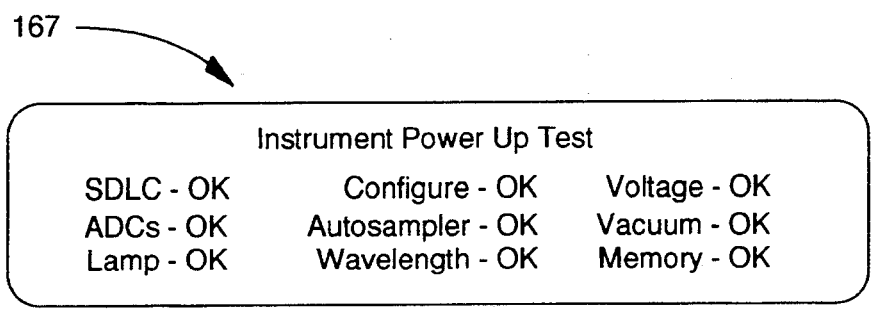
FIG. 10 is a power up test menu for the instrument of the invention.

FIG. 9 is a diagram of pre-stored Menus and information displays for the Model 270A-HT instrument. Box 165 represents a Power Up menu which appears when the operator turns on the power to the instrument, and the instrument in response sequences through a pre-stored self-diagnostic sequence. At the end of the sequence the control lists on the screen in a display array 187 shown in FIG. 10 the tested parameters and functions with results of each. A passing result is listed as "OK", and a failure is listed as "BAD" If there is a failure, the control will not allow access to operating sequences.

Box 189 in FIG. 9 represents a Start Up screen, which simply displays the Manufacturer's name (Applied Biosystems of Foster City, Calif.), the Model Number of the instrument, and the Version Number for the operating control software.

Figure 11:
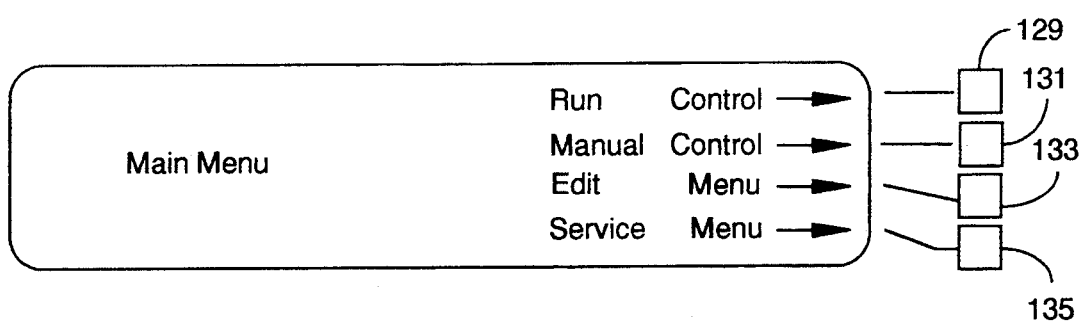
FIG. 11 shows the Main Menu for control of the instrument of the invention.

Box 171 in FIG. 9 represents the Main Menu, which is the starting point for all instrument operations. The Main Menu screen 173 is shown in FIG. 11, and includes annotation for each of the four soft keys on the control panel illustrated in FIG. 8. For clarity, the four soft keys are shown to the right of the screen in FIG. 11. The menu diagram of FIG. 9 shows four main branches from the Main Menu, these being box 175, the Run Control Menu; box 177, the Manual Control Menu; Box 179, the Edit Menu; and box 181, the Service Menu. These are the four menus reachable from the main menu, and to reach one of the four requires that the appropriate soft key be pressed.

Figure 12:
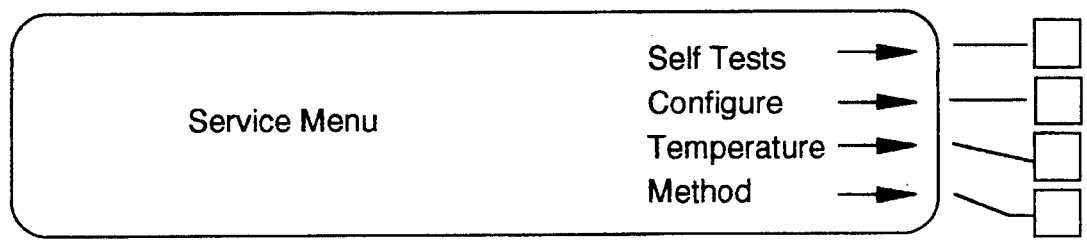
FIG. 12 shows the Service Menu.

The Service Menu, accessible from the Main Menu by the associated soft key, is shown in FIG. 12, with choices associated with the soft keys for four service screens. Self Tests presents a screen for choosing self-test of system electronics or hardware. Configure displays a screen for setting the current time and date, to set contact closure mode, and to set the load type to either gel or capillary. Temperature displays a screen for calibrating the oven temperature. Method displays a screen for changing default values on the Edit Method menu, which is a menu for editing methods.

Figure 13:
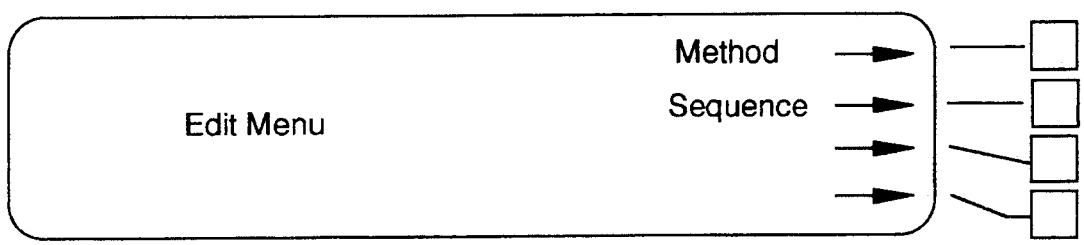
FIG. 13 shows the Edit Menu.

The Edit Menu, accessible from the Main Menu by pressing the associated soft key, is shown in FIG. 13, and presents two choices: Method and Sequence. To edit a method, the operator selects Method with the associated soft key, and to edit a sequence the operator selects Sequence.

Figure 14:
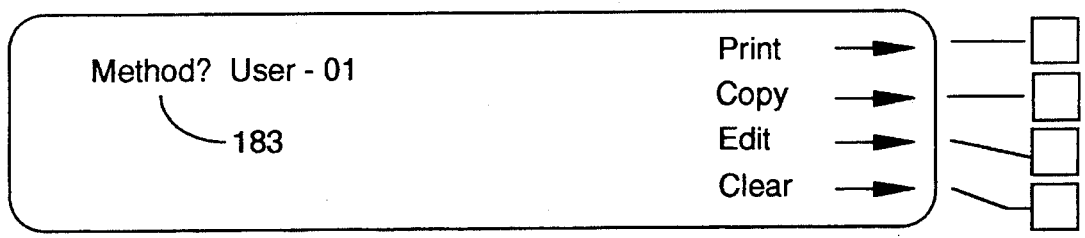
FIG. 14 shows the Edit Method Menu.

FIG. 14 is the Edit Method menu. From the Edit Method menu the operator can print, copy, edit, or clear a method. The operator may make Method field 183 active with the Previous/Next keys on the control panel of FIG. 8, and cycle through the available User Methods from 01 to 10. These editing techniques are common to all screens. With a method displayed, such as User—01 as in FIG. 14, the operator can print the method by the Print soft key. The printed report will list all of the cycles that make up the method in order, and the parameters for each cycle.

Figure 15:
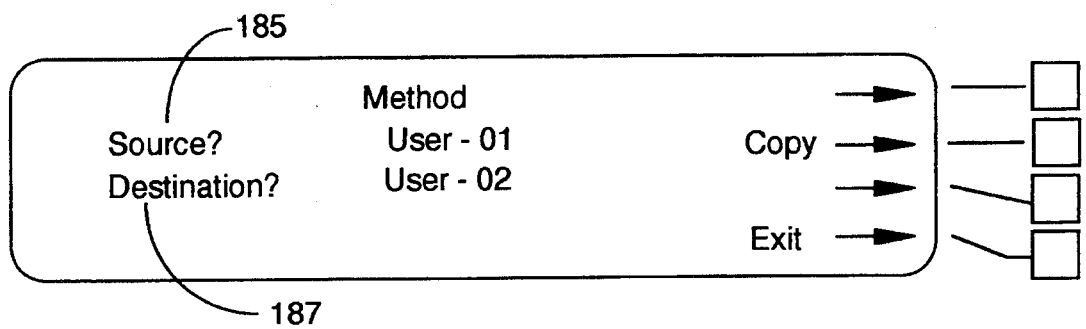
FIG. 15 shows the Copy Method Menu.

The Copy soft key from the Edit Method menu presents the Copy Method menu shown in FIG. 15. To copy, the operator activates Source field 185, cycles through the available selections until the field reads out the method the operator wants to copy, then does the same with Destination field 187 to see the destination for the copy. Pressing the Copy soft key then copies the Source method to the Destination method. The Copy function allows an operator to set up new methods that are similar to existing methods without starting each time from scratch. Exit sends control back to the Edit Method menu.

From the Edit Method menu of FIG. 14 the operator can clear a method by displaying a method number and pressing the Clear soft key. The method of that number will then have default values substituted for the method.

Figure 16:
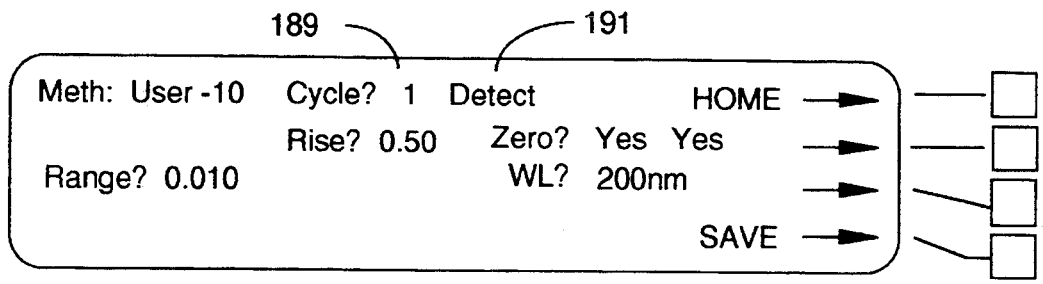
FIG. 16 shows the Cycle Editing Screen.

The Edit soft key from the Edit Method menu displays a Cycle Editing screen for the Method selected in the Edit Method menu. The Cycle Editing screen is shown in FIG. 16 for Cycle 1 of method User—10. The operator can select Cycle? field 189 and step through numbers for up to 9 cycles, set the cycle type in the type field 191, and set the required parameters for the cycle type by stepping to the appropriate fields and entering values or parameters from existing lists. At the end of defining a cycle, the Home soft key sends the active field back to the Cycle? field. When the operator has finished all the cycle definition, the SAVE softkey records the method and sends control back to the Edit Method menu.

Figure 17:
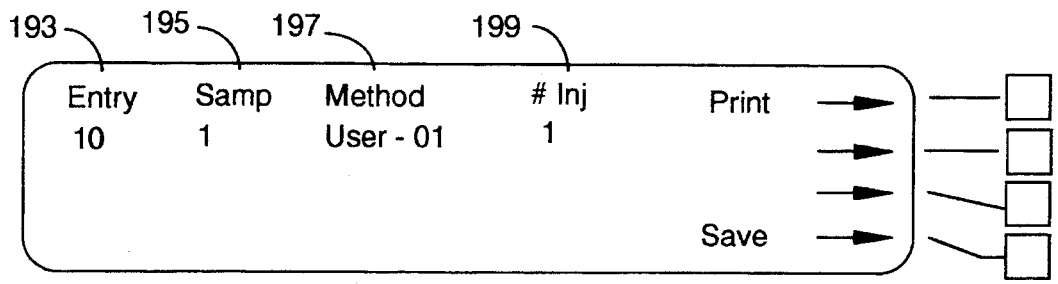
FIG. 17 shows the Edit Sequence Menu.

From the Edit menu of FIG. 13 the operator can choose to edit a sequence rather than a method, by pressing the Sequence Soft key. In response, the control displays the Edit Sequence menu shown in FIG. 17. This menu is for establishing an order of methods in a sequence to be carried out by the instrument automatically. The operator can define a sequence of up to 100 methods by selecting entry numbers 1-100 in Entry field 193, assigning a sample vial number in Samp field 195 and a method in Method field 197, and specifying a number of injections to be made from the vial in the Samp field in the #Inj field 199.

The Print soft key in the Edit Sequence menu causes the instrument to print a sequence report. After all the definition of the sequence for an automatic run is done, the Save soft key saves the defined sequence.

Figure 18:
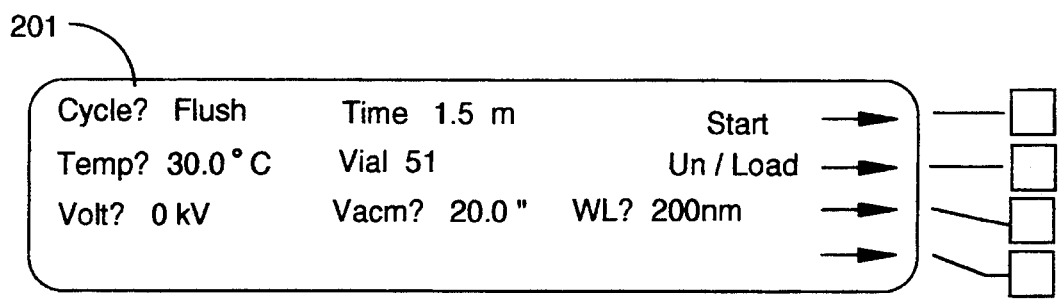
FIG. 18 is a Manual Control Menu for the Flush Cycle.

From the Main Menu shown in FIG. 11, Manual Control menus are accessible by pressing the Manual Control soft key. A Manual Control menu for the Flush cycle is shown in FIG. 18. The operator can select a cycle, enter parameters, and run the cycle without having to run a method. There are similar screens to the Flush cycle screen of FIG. 18 for the other cycles, and all are accessible by selecting Cycle? field 201.

With the Un/Load soft key the operator can move the Autosampler carousel out for loading a new sample (or for any other reason), and move in back in again by pressing the same soft key again. When all is set, the operator can run the cycle by pressing the Start soft key.

Figure 19A:
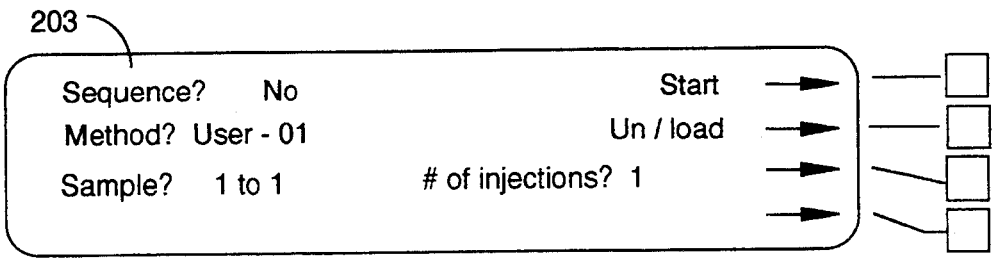
FIG. 19A is a Run Control Menu for the instrument of the invention.
Figure 19B:
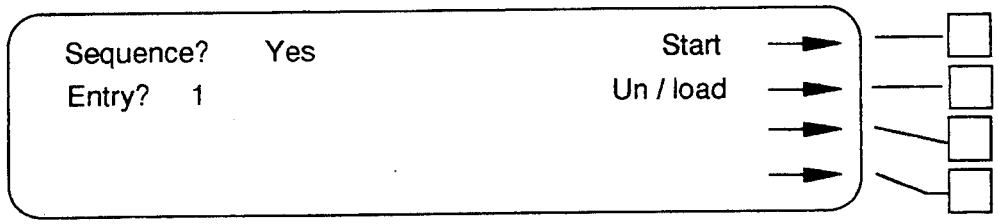
FIG. 19B is another menu involved in run control.

When the operator presses the soft key for Run Control from the Main Menu, the control displays the menu shown in FIG. 19A, for operating the instrument in fully automatic mode. Sequence? field 203 has Yes and No selections displayed by the Prev. or Next keys. To run the defined sequence the operator sets Sequence? to Yes. The control then displays the menu shown in FIG. 19B. The operator can press the Un/Load soft key to extend the carousel (for any of a number of reasons and again to retract the carousel. The operator presses the Start soft key to begin the run.

Figure 19C:
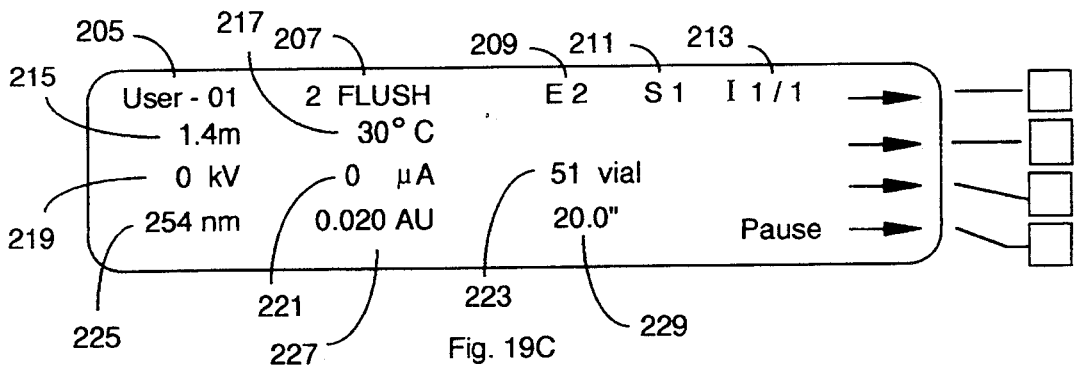
FIG. 19C is a screen for monitoring run status.

The control displays the screen shown in FIG. 19C after the Start key is pressed to monitor the run status. The operator can press the Pause soft key at any time during the run to cause the control to stop the run and wait for a restart by the Continue key on the control panel.

In FIG. 19C, field 205 displays the current method during a run, field 207 the cycle (number and type), field 209 the entry number of the sequence, field 211 the sample number, field the current injection number of the total injections, field 215. the time into the run, field 217 the temperature, field 219 the voltage, field 221 the run current, field 223 the vial number being used, field 225 the detector wavelength, field 227 the detector absorbance, and field 229 the vacuum level at the outlet buffer reservoir.

Figure 19D:
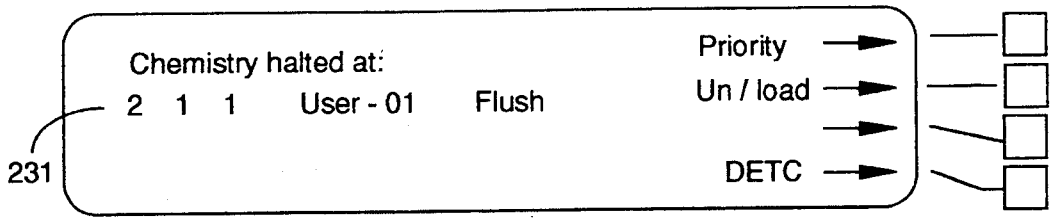
FIG. 19D is a pause screen in Run Control.

If the operator presses the Pause soft key during a run, the control displays the Pause screen shown in FIG. 19D. Row 281 displays the instrument status at Pause. The soft keys allow the operator to go from pause to a Priority menu shown in FIG. 19E to run a priority sample, to extend and retract the carousel (Un/Load soft key), or to go directly to a Detector menu that shows the status of the on-line detector.

Figure 19E:
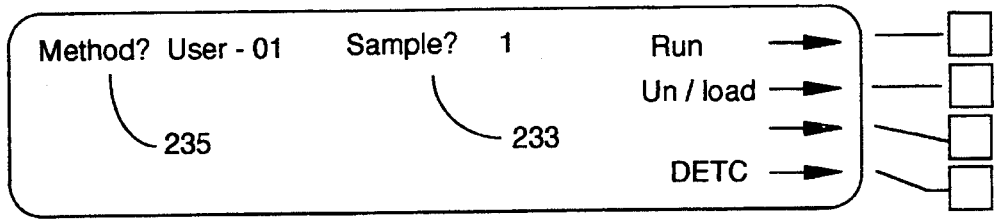
FIG. 19E is a priority menu.

The Priority menu of FIG. 19E is for selecting a priority sample in field 233 and running it. The operator can also select a priority method in field 235. When the Run soft key is pressed in the priority menu, the current injection in the running series is first completed, then the priority sample and method are run, after which the series resumes at the next injection.

In a typical procedure, after power up and verifying the operation of the system, an operator uses the menu system to set up the sequence of methods and the operating parameters for the samples to be run, then loads the tray of samples and buffers into the carousel. There are, as described above, several kinds of electrophoresis capable of being performed by the apparatus of the invention, and a wide variety of operating parameters and conditions, controllable in the system, suited to different electrophoretic procedures. After set up and loading, it is only required to initiate the rerun, and the system automatically follows the stored operating instructions for the sequence.

The above descriptions detail most the procedures for controlling the operations of the instrument, and the diagram of FIG. 9 shows the hierarchical nature of the menus and screens. It will be evident to those with skill in the art that other menus may be prepared, stored, and incorporated into the control structure. It will be apparent as well that there are many changes that might be made in the apparatus without departing from the spirit and scope of the invention. For example, there are a number of different kinds and arrangement of drives that may be used to position the autosampler carousel, such as X-Y positioning apparatus. There are also equivalent ways to actuate the electrode and capillary end to access sample and buffer vials in the autosampler.

There are many ways the apparatus according to the invention may be used in electrophoresis, and many have been detailed above as examples, but certainly not all. The provision of apparatus for both electrokinetic and hydrodynamic technique simultaneously, or individually, provides a very broad range of operating possibilities.

Another example of changes that might be made is in the design and treatment of the septum for closing vials while permitting entry of capillaries and electrodes. There are other flexible materials that could be used for the septum than the material described above, and similarly alterations in design that might be made within the scope of the invention. For example, the wedge-shaped opening may have an included angle other than 44 degrees, although 44 degrees has been found to be preferable. Also, there are other ways the septum may be treated with a lubricant. The specific method described above is exemplary of treatment to reduce friction for the septum.

What is claimed is:

1. A capillary electrophoresis instruments having an external enclosure, comprising:
   a carrier within the enclosure configured for carrying a first end of an electrophoresis capillary and a first electrode positioned side-by-side relative to one another;
   a carrier drive configured for translating the carrier vertically at a load position for inserting the first end of the capillary and the first electrode into a container for liquid, and for withdrawing therefrom;
   an outlet station within the enclosure configured for holding a buffer reservoir and for positioning a second end of the capillary and a second electrode in the second buffer reservoir;
   a rotary carousel having a circular array of support positions for liquid containers; and
   a delivery apparatus configured for supporting and moving the rotary carousel from without the enclosure to within the enclosure and from within the enclosure to without the enclosure, and for rotating the carousel within the enclosure, presenting the support positions for liquid containers individually at the load position.

2. A capillary electrophoresis instrument as in claim 1 further comprising a detector positioned between the load position and the outlet station, the detector configured for monitoring separated sample bands passing along a capillary tubing.

3. A capillary electrophoresis instrument as in claim 1 further comprising a control system including a microcontroller for operating the delivery apparatus and controlling electrophoresis operations, and a user interface for entering commands and selecting operational sequences.

4. A capillary electrophoresis instrument as in claim 3 wherein the control system is configured for powering the first and second electrodes with the first electrode and the first end of the capillary immersed in a sample to perform electrokinetic injection of sample material into the first end of the capillary.

5. A capillary electrophoresis instrument as in claim 1 wherein the rotary carousel comprises a removable tray having the circular array of support positions for liquid containers, the removable tray removable and replaceable with the rotary carousel supported on the delivery apparatus outside the enclosure.

6. A capillary electrophoresis instrument as in claim 1 wherein the rotary carousel comprises plural concentrically-arranged circular arrays of support positions for liquid containers, and the delivery apparatus is configured to move the centerpoint of the rotary carousel within the enclosure, and to rotate the carousel, to present the support positions for liquid containers in each circular array at the load position.

7. A capillary electrophoresis instrument as in claim 6 wherein the rotary carousel comprises a removable tray having the plural concentrically-arranged circular arrays of support positions for liquid containers, the removable tray removable and replaceable with the rotary carousel supported on the delivery apparatus outside the enclosure.

8. A capillary electrophoresis instrument as in claim 1 wherein said rotary carousel comprises a temperature adjustment system for maintaining sample materials in liquid containers supported by the carousel at other than ambient temperature.

9. A capillary electrophoresis instrument as in claim 1 further comprising a temperature control system for maintaining a portion of the volume within the enclosure at other than ambient temperature.

10. A capillary electrophoresis instrument as in claim 1 wherein the carrier comprises adjustable holders configured to provide adjustment of the physical relationship of the first end of the capillary and the first electrode.

11. A capillary electrophoresis instrument as in claim 1 wherein the outlet station is configured for holding a sealed second buffer reservoir with the second end of the capillary and the second electrode immersed in a buffer solution held in the sealed second buffer reservoir, and the capillary electrophoresis instrument further comprises a vacuum system for creating a variable vacuum over a buffer solution held in the sealed buffer reservoir, providing a variable pressure differential across the first end and the second end of the capillary, promoting flow in the capillary toward the second end for providing controlled injection of sample material at the first end of the capillary.

12. A capillary electrophoresis instrument as in claim 11 further comprising a pressurizing system for creating a relative positive pressure in the sealed buffer reservoir, promoting flow in the capillary toward the first end for providing expulsion of separated sample bands from the capillary into individual ones of liquid containers supported on the rotary carousel.

13. A capillary electrophoresis instrument as in claim 1 comprising liquid containers for sample material supported on the carousel, individual ones of the liquid containers sealed with a duck-billed septum for allowing easy entry of the first end of the capillary and the first electrode while minimizing exposure of sample material in the liquid container, the duck-billed septum adapted for sealing to an opening of the liquid container and having a wedge-shaped opening comprising two opposing, inwardly-sloping surfaces extending toward the interior of the container, the inwardly-sloping surfaces ending in a slit for allowing penetration of the first end of the capillary and the first electrode side-by-side.

14. A capillary electrophoresis instrument comprising:

a carrier configured for carrying a first end of an electrophoresis capillary and the first electrode positioned side-by-side relative to one and;

a carrier drive configured for translating the carrier vertically at a load position for inserting a first end of the capillary and the first electrode into a container for liquid, and for withdrawing therefrom;

an outlet station configured for holding a buffer reservoir and for positioning a second end of the capillary and a second electrode in the buffer reservoir;

a delivery apparatus configured for supporting and moving liquid containers to and away from the load position; and a control system configured for powering the first and second electrodes with the first electrode and the first end of the capillary immersed sample in a liquid container in a to perform electrokinetic injection of sample material into the first end of the capillary.

15. A capillary electrophoresis instrument as in claim 14 further comprising an external enclosure, and wherein the delivery apparatus comprises a rotary carousel having a circular array of support positions for liquid containers, and a carousel operator apparatus for supporting and translating the rotary carousel from without the enclosure to within the enclosure and from within the enclosure to without tile enclosure, and for rotating the carousel within the enclosure, presenting the support positions for liquid containers individually at the load position.

16. A capillary electrophoresis instrument as in claim 15 wherein the rotary carousel comprises a removable tray having the circular array of support positions for liquid containers, the removable tray removable and replaceable with the rotary carousel supported on the carousel operator apparatus outside the enclosure.

17. A capillary electrophoresis instrument as in claim 15 wherein the rotary carousel comprises plural concentrically-arranged circular arrays of support positions for liquid containers, and the carousel operator apparatus is configured to move the centerpoint of the rotary carousel within the enclosure, and to rotate the carousel, to present the support positions for liquid containers in each circular array at the load position.

18. A capillary electrophoresis instrument as in claim 17 wherein the rotary carousel comprises a removable tray having the plural concentrically-arranged circular arrays of support positions for liquid containers, the removable tray removable and replaceable with the rotary carousel supported on the carousel operator apparatus outside the enclosure.

19. A capillary electrophoresis instrument as in claim 15 wherein said rotary carousel comprises a temperature adjustment system for maintaining sample materials in liquid containers supported by the carousel at other than ambient temperature.

20. A capillary electrophoresis instrument as in claim 15 further comprising a temperature control system for maintaining a portion of a volume within the enclosure at other than ambient temperature.

21. A capillary electrophoresis instrument as in claim 14 further comprising a detector positioned between the load position and the outlet station, the detector configured for monitoring separated sample bands passing along a capillary tubing.

22. A capillary electrophoresis instrument as in claim 14 wherein the control system comprises a microcontroller for operating the delivery apparatus and controlling electrophoresis operations, and a user interface for entering commands and selecting operational sequences.

23. A capillary electrophoresis instrument as in claim 14 wherein the carrier comprises adjustable holders configured to provide adjustment the first end of the capillary and the first electrode.

24. A capillary electrophoresis instrument as in claim 14 wherein the outlet station is configured for holding a sealed second buffer reservoir with the second end of the capillary and the second electrode immersed in a buffer solution held in the sealed second buffer reservoir, and the capillary electrophoresis instrument further comprises a vacuum system for creating a variable vacuum over a buffer solution held in the sealed buffer reservoir, providing a variable pressure differential across the first end and the second end of the capillary, promoting flow in the capillary toward the second end for providing controlled injection of sample material at the first end of the capillary.

25. A capillary electrophoresis instrument as in claim 14 further comprising a pressurizing system for creating a relative positive pressure in the sealed buffer reservoir, promoting flow in the capillary toward the first end for providing expulsion of separated sample bands from the capillary into individual ones of liquid containers supported on the rotary carousel.

26. A capillary electrophoresis instrument as in claim 14 comprising liquid containers for sample material supported on the carousel, individual ones of the liquid containers sealed with a duck-billed septum for allowing easy entry of the first end of the capillary and the first electrode while minimizing exposure of sample material in the liquid container, the duck-billed septum adapted for sealing to an opening of the liquid container and having a wedge-shaped opening comprising two opposing, inwardly-sloping surfaces extending toward the interior of the container, the inwardly-sloping surfaces ending in a slit for allowing penetration of the first end of the capillary and the first electrode side-by-side.

* * * * *